(12) United States Patent
Cassidy et al.

(10) Patent No.: US 9,885,147 B2
(45) Date of Patent: Feb. 6, 2018

(54) REPRODUCIBLE SAMPLE PREPARATION METHOD FOR QUANTITATIVE STAIN DETECTION

(71) Applicant: UNIVERSITY OF SOUTH CAROLINA, Columbia, SC (US)

(72) Inventors: Brianna Cassidy, Columbia, SC (US); Zhenyu Lu, Columbia, SC (US); Katherine Witherspoon, Columbia, SC (US); Alena Bensussan, Monroe, CT (US); Jennifer Martin, Pelion, SC (US); Stephanie Dejong, Ripon, CA (US); Michael Myrick, Columbia, SC (US); Stephen L. Morgan, Columbia, SC (US); Wayne L. O'Brien, Port Arthur, TX (US); MacKenzie Meece-Rayle, Austin, TX (US)

(73) Assignee: University of South Carolina, Columbia, SC (US)

( * ) Notice: Subject to any disclaimer, the term of this patent is extended or adjusted under 35 U.S.C. 154(b) by 103 days.

(21) Appl. No.: 15/136,217

(22) Filed: Apr. 22, 2016

(65) Prior Publication Data

US 2016/0313225 A1    Oct. 27, 2016

Related U.S. Application Data

(60) Provisional application No. 62/152,065, filed on Apr. 24, 2015.

(51) Int. Cl.
*G01N 33/49* (2006.01)
*D06M 15/248* (2006.01)
*D06M 23/16* (2006.01)
*D06N 3/06* (2006.01)
*G01N 1/28* (2006.01)

(52) U.S. Cl.
CPC .......... *D06M 15/248* (2013.01); *D06M 23/16* (2013.01); *D06N 3/06* (2013.01); *G01N 1/28* (2013.01)

(58) Field of Classification Search
CPC ....... D06N 7/0094; B05D 3/007; G01N 33/49
USPC .................................................. 427/282, 256
See application file for complete search history.

(56) References Cited

U.S. PATENT DOCUMENTS

| | | |
|---|---|---|
| 3,562,524 A | 2/1971 | Moore et al. |
| 3,684,867 A | 8/1972 | Acker |
| 3,783,284 A | 1/1974 | McCormack |
| 4,201,914 A | 5/1980 | Perren |
| 4,292,272 A * | 9/1981 | Kitajima .............. G01N 33/525 422/428 |

(Continued)

OTHER PUBLICATIONS

Andrasko, J., "The estimation of the age of bloodstains by HPLC analysis," *J. Forensic. Sci.*, (1997) 42 (4) pp. 601-607.

(Continued)

*Primary Examiner* — Cachet I Sellman
(74) *Attorney, Agent, or Firm* — Dority & Manning, PA

(57) ABSTRACT

A stain-barrier is described along with methods of its application to a fabric. The stain barrier can be applied to fabric samples and limits the amount of fabric with which deposited liquid is able to interact. This stain barrier reduces unwanted variability between samples of different dilution or fabric type so that limits of stain detection can be assigned more accurately and precisely and stain detection techniques can be transparently compared.

14 Claims, 6 Drawing Sheets

(56) References Cited

U.S. PATENT DOCUMENTS

| | | | |
|---|---|---|---|
| 4,333,008 A | | 6/1982 | Misek |
| 4,832,699 A | * | 5/1989 | Choi .................. D06P 1/65118 |
| | | | 8/611 |
| 5,179,422 A | | 1/1993 | Peterson |
| 5,247,185 A | | 9/1993 | Herrera et al. |
| 5,312,521 A | | 5/1994 | Fraas et al. |
| 5,330,817 A | * | 7/1994 | Arnott .................... A61F 5/485 |
| | | | 428/85 |
| 5,504,332 A | | 4/1996 | Richmond et al. |
| 5,900,634 A | | 5/1999 | Soloman |
| 5,945,676 A | | 8/1999 | Khalil et al. |
| 5,946,088 A | | 8/1999 | Aldridge |
| 6,260,997 B1 | | 7/2001 | Claybourn et al. |
| 6,370,327 B1 | | 4/2002 | Seguy et al. |
| 6,490,035 B1 | | 12/2002 | Folestad et al. |
| 6,504,943 B1 | | 1/2003 | Sweatt et al. |
| 6,517,230 B1 | | 2/2003 | Afnan et al. |
| 6,753,190 B1 | * | 6/2004 | Okada ................. G01N 33/543 |
| | | | 435/4 |
| 6,776,517 B2 | | 8/2004 | Afnan et al. |
| 6,849,460 B2 | | 2/2005 | McFarland et al. |
| 7,123,360 B2 | | 10/2006 | Treado et al. |
| 7,417,228 B2 | | 8/2008 | Belov |
| 7,489,252 B2 | | 2/2009 | Long et al. |
| 7,595,734 B2 | | 9/2009 | Long et al. |
| 7,623,235 B2 | | 11/2009 | Ho et al. |
| 7,623,237 B1 | | 11/2009 | Liphardt et al. |
| 7,671,975 B2 | | 3/2010 | Mangan et al. |
| 2004/0239923 A1 | | 12/2004 | Adams et al. |
| 2005/0032235 A1 | | 2/2005 | Tummala et al. |
| 2005/0062006 A1 | | 3/2005 | Wilfert |
| 2006/0060278 A1 | | 3/2006 | Treado et al. |
| 2006/0106317 A1 | | 5/2006 | McConnell et al. |
| 2007/0021670 A1 | | 1/2007 | Mandelis et al. |
| 2007/0152154 A1 | | 7/2007 | DeCamp et al. |
| 2007/0201136 A1 | | 8/2007 | Myrick et al. |
| 2008/0094616 A1 | | 4/2008 | Tanaka |
| 2008/0225303 A1 | | 9/2008 | Lampalzer |
| 2008/0276687 A1 | | 11/2008 | Myrick et al. |
| 2009/0073433 A1 | | 3/2009 | Myrick et al. |
| 2009/0140144 A1 | | 6/2009 | Myrick et al. |
| 2009/0216504 A1 | | 8/2009 | Myrick et al. |
| 2009/0219512 A1 | | 9/2009 | Myrick et al. |
| 2009/0219538 A1 | | 9/2009 | Myrick et al. |
| 2009/0219539 A1 | | 9/2009 | Myrick et al. |
| 2009/0219597 A1 | | 9/2009 | Myrick et al. |
| 2009/0245321 A1 | | 10/2009 | Ringermacher |
| 2009/0250613 A1 | | 10/2009 | Myrick et al. |
| 2009/0303471 A1 | | 12/2009 | Treado et al. |
| 2009/0318815 A1 | | 12/2009 | Barnes et al. |
| 2010/0042348 A1 | | 2/2010 | Bakker |
| 2010/0195105 A1 | | 8/2010 | Myrick et al. |
| 2010/0265320 A1 | | 10/2010 | Treado et al. |
| 2011/0007774 A1 | | 1/2011 | Hatcher |
| 2011/0090342 A1 | | 4/2011 | Myrick et al. |
| 2013/0109024 A1 | * | 5/2013 | Rajagopalan ........ G01N 1/2813 |
| | | | 435/6.12 |
| 2013/0230821 A1 | | 9/2013 | Brown |
| 2013/0331666 A1 | * | 12/2013 | Miller .................. A61B 5/1405 |
| | | | 600/309 |
| 2015/0094678 A1 | * | 4/2015 | O'Brien .............. A61F 13/8405 |
| | | | 604/367 |

OTHER PUBLICATIONS

Blum, etal.; "A new high-performance reagent and procedure for latent bloodstain detection based on luminol chemiluminescence," *Canadian Society of Forensic Science* (2006) 39(3) pp. 81-100.

Botonjic-Sehic, etal; "Forensic application of near infrared spectroscopy: aging of bloodstains," *Spectroscopy* (2009) 24 pp. 42-48.

Bremmer, etal; "Forensic quest for age determination of bloodstains," *Forensic Sci. Int.*, (2012) 216 pp. 1-11.

Bruno A. Olshausen, "Aliasing"—handout prepared and distributed for PSC 129 at the University of California, Berkeley, dated 2000, retrieved online from http://redwood.berkeley.edu/bruno/npb261/aliasing.pdf Jun. 5, 2015.

Budowle, etal.; "The presumptive reagent fluorescein for detection of dilute bloodstains and subsequent STR typing of recovered DNA," *J Forensic Sci* (2000) 45(5) pp. 1090-2.

Edelman, etal.; "Identification and age estimation of blood stains on colored backgrounds by near infrared spectroscopy," *Forensic Sci. Int.*, (2012) 220 pp. 239-244.

Egan, etal.; "Measurement of carboxyhemoglobin in forensic blood samples using UV/VIS spectrometry and improved principal component regression," *Applied Spectroscopy* (1999) 53(2) pp. 218-225.

Finnis, J.; Lewis, J.; Davidson, A. Comparison of methods for visualizing blood on dark surfaces. Science and Justice 2013:53:178-186.

Garofano, etal; "A comparative study of the sensitivity and specificity of luminol and fluorescein on diluted and aged bloodstains and subsequent STRs typing," *International Congress Series* (2006) 1288 pp. 657-9.

Gnyaneshwari; "An evaluation of luminol formulations and their effect on DNA profiling," *Int J Legal Med* (2013) 127 pp. 723-9.

Hanson et al.; "A blue spectral shift of the hemoglobin soret band correlates with the age of dried bloodstains," *Plos ONE* (2010) 5 [ e12830].

Lu, etal.; "Using Fourier transform infrared spectroscopy to estimate blood age under different environmental conditions," Abstract No. 2170-6; Univ. of South Carolina; Mar. 11, 2015 (abst. only).

Inoue, etal.; "A new marker for estimation of bloodstain age by high performance liquid chromatography," *Forensic Sci. Int.*, (1992) 57 pp. 17-27. Abst only.

Inoue, etal; "Identification of fetal hemoglobin and simultaneous estimation of bloodstain age by high-performance liquid chromatography," *Int. J. Legal Med.*, (1991) 104 pp. 127-131.

Kind, etal.; "Estimation of the age of dried blood stains by a spectrophotometric method," *Forensic Sci.* (1972) 1 pp. 27-54.

Matsuoka, etal.; "Estimation of bloodstain age by rapid determinations of oxyhemoglobin by use of oxygen-electrode and total hemoglobin," *Biol. Pharm. Bull.* (1995) 18 pp. 1031-1035.

Mauerer, A., "Secondary Structural Change of Spray Dried Proteins with Fourier Transform Infrared Spectroscopy," *Ph. D. Dissertation, Friedrich-Alexander University Erlangen-Nuremberg, Erlangen, Germany*.

Mccutcheon, J. N., "Estimation of the age of bloodstains on polymer substrates by infrared spectroscopy," *University of South Carolina*, 2010.

Middlestead, etal.; "Sensitivity of the luminol test with blue denim," *J Forensic Sci* (2010) 55(5) pp. 1340-2.

PCT International Search Report for PCT/US11/35156 dated Sep. 2, 2011, 2 pages.

PCT International Search Report for PCT/US2011/035149 dated Aug. 22, 2011, 2 pages.

Schwarz, F., "Quantitative analysis of catalase und peroxidase in bloodstain," *Int. J. Legal Med.*, (1937) 27 pp. 1-34.

Seashols, etal.; "A comparison of chemical enhancements for the detection of latent blood," *J. Forensic Sci* (2013) 58(1), pp. 130-3.

Smith, B., "Infrared spectral interpretation," *CRC press*, Washington D.C., 1999.

Su, etal.; "Mechanics of forced unfolding of proteins," *Acta Biomater* (2009).

Tobe, etal.; "Evaluation of six presumptive tests for blood, their specificity, sensitivity, and effect on high molecular-weight DNA," *J Forensic Sci* (2007) 52(1) pp. 102-109.

Webb, et al.; "A comparison of the presumptive luminol test for blood with four non-chemiluminescent forensic techniques," *Luminescence* (2006) 21(4) pp. 214-220.

Webb; "Luminol vs Bluestar: A Comparison Study of Latent Blood reagents," [Internet]. Available from: http://www.bluestar-forensic.com/pdf/en/St_Louis_comparison_study.pdf 6 pages.

* cited by examiner

REPRODUCIBLE SAMPLE PREPARATION METHOD FOR QUANTITATIVE STAIN DETECTION

CROSS REFERENCE TO RELATED APPLICATION

This application claims filing benefit of U.S. Provisional Patent Application Ser. No. 62/152,065, having a filing date of Apr. 24, 2015, which is incorporated herein by reference for all purposes.

GOVERNMENT SUPPORT CLAUSE

This invention was made with government support under 2011-IJ-CX-K055 awarded by National Institute of Justice. The government has certain rights in the invention.

BACKGROUND

Blood stains, which are among the traces encountered most frequently at crime scenes, are important for potential extraction and amplification of DNA for suspect identification, as well for spatter pattern analysis to reveal a sequence of events. Estimating the age of blood stains with good accuracy and precision has been an elusive goal for forensic investigations. Estimates of blood stain age can contribute to verify witness' statements, limit the number of suspects and confirm alibis.

Blood is composed of plasma (~53%), platelets (<1%), white blood cells (~1%), and red blood cells (~45%). Hemoglobin, an oxygen carrying protein, makes up about 90% of dried blood content. In healthy blood, hemoglobin exists in two forms: deoxyhemoglobin (Hb), which is without oxygen, and oxyhemoglobin ($HbO_2$), which is saturated with oxygen. When blood is exposed to air, Hb is completely saturated with oxygen and converts to $HbO_2$. $HbO_2$ will irreversibly oxidize to methemoglobin (met-Hb). After that, met-Hb will denature to hemichrome (HC). During these process, changes in the secondary structure of the protein will take place. Hemoglobin is about 80% α-helix type proteins, while the other 20% are unordered coils. After aging, hemoglobin contains 60% α-helix type proteins, 30% β-sheet type proteins and 10% other types.

Many stain detection techniques exist (luminol, Bluestar®, fluorescein, hemascein, etc.). However, their limits of detection are not agreed upon and they are unable to be quantitatively compared to one another due to the inability to reproducibly create stain samples. Fourier Transform Infrared (FT-IR) spectrometry was developed to overcome the limitations encounter with the slow scanning of dispersive instruments. FT-IR employed an interferometer to produce a interferogram, which allows all of the infrared frequencies been detected simultaneously. The signal can be measured on the order of one second or so. The measured signal is digitized and then transformed from the time domain to the frequency domain. The infrared spectrum is then presented as a plot of absorbance vs. frequency.

However, one main issue still exists. The stain samples are currently made without regard to the effects of different stain dilutions and substrate properties. Thus, stain detection limits are imprecisely assigned to stain detection techniques, making it difficult to compare stain detection techniques to one another.

Further, many recent studies have attempted to assign limits of detection and/or compare the ability of different stain detection techniques. For studies like these to be successful, a method needs to exist which allows reproducible creation of stain samples. Currently, dilutions of stains are made and applied in constant aliquots, but no consideration is given to the effect diluting a liquid has on its behavior when applied to fabric. Generally, the more dilute a liquid, the further the liquid spreads when applied to a substrate. Additionally, consideration has not been given to the affect different substrates have on the spread of applied liquids. For example, a liquid of the same dilution and volume will spread to a smaller area on densely packed cotton than on a loosely woven silk. Both aforementioned phenomena affect the true dilution of the stain. The absence of a technique which controls the liquid-fabric interaction and allows production of reproducible stains has made experiments of this nature hugely imprecise. Consequently, vast ranges of detection limits have been assigned to various stain detection techniques. For example, luminol has been reported to have a bloodstain detection limit of five-millions times dilute (5) to one-hundred times dilute (4).

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures, in which.

Figure 1A:
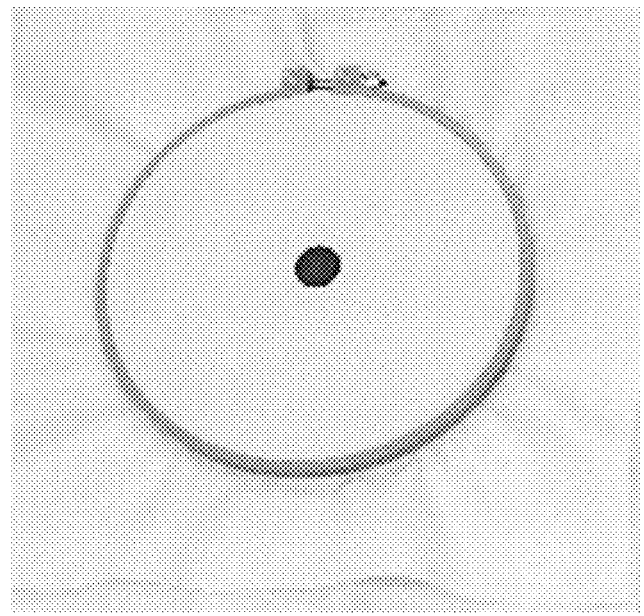
FIG. 1a shows a cotton fabric having a stain applied to a target area protected by an inert barrier coating.

Repeat use of reference characters in the present specification and drawings is intended to represent the same or analogous features or elements of the present invention.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

A stain-barrier is generally provided, along with methods of its application to a fabric. The stain barrier is easily applied to fabric samples, and limits the amount of fabric with which deposited liquid is able to interact. This stain barrier greatly reduces unwanted variability between samples of different dilution or fabric type so that limits of stain detection can be assigned more accurately and precisely and stain detection techniques can be transparently compared. Thus, the effect of stain-dilution and substrate is minimized by application of the stain-barrier to the fabric. The stain barrier allows more replicable stain samples to be made, so that stain detection techniques can be accurately compared for the first time.

The presently disclosed methods allow liquid stains to be created on fabric in a reproducible, constant manner so as to limit and hold constant the amount of fabric with which the liquid may interact. In one embodiment, an inert barrier layer is applied onto the fabric to prevent the liquid from interacting with fabric outside the intended area (i.e., the sample area). The stain barrier created using this method insures that each stain spreads within a replicable area of the fabric, thus reducing variability between samples where different dilutions of stain and different fabric substrates are implemented. Now that variation due to sample preparation can be reduced, variation due to dilution, substrate and detection response can be more clearly observed. Thus, more accurate limits of detection can to be determined for stain detection techniques and for the first time, fair comparison of stain detection techniques to one another.

Figure 2:
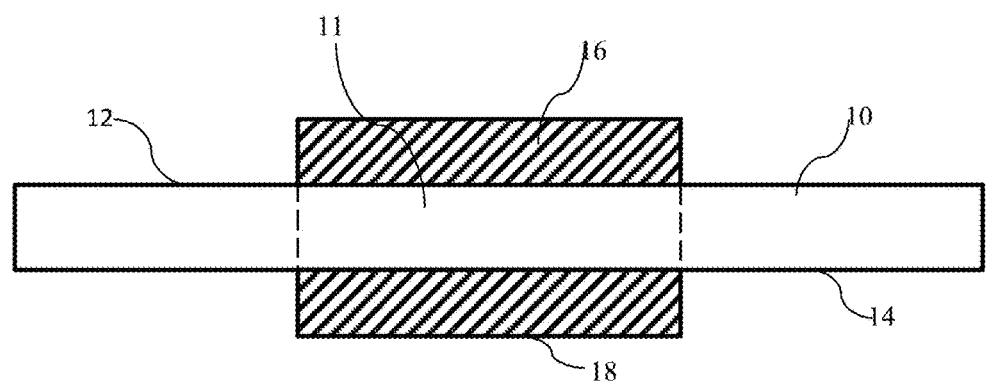
FIG. 2 is a cross-sectional view of an exemplary fabric having a mask positioned on either surface of the fabric protecting the sample area when applying the inert barrier composition.

Referring to FIG. 2, a fabric 10 is shown defining a first surface 12 and an opposite second surface 14. The fabric can be a woven or nonwoven fabric containing fibers. Any suitable material can be utilized to form the fabric, such as cotton fibers, nylon fibers, polyester fibers, silk fibers, etc.

The first mask 16 is positioned on the first surface 12 to cover a portion 11 of the fabric. Similarly, a second mask 18 is positioned on the second surface 14 to cover substantially the portion 11 of the fabric. The portion 11 of the fabric 10 protected by the first mask 16 and the second mask 18 will correspond to the sample area formed after applying and drying the inert barrier composition to form an inert barrier coating. Although shown utilizing two masks 16, 18, it is to be understood that a single mask could be utilized in certain embodiments.

In one embodiment, pressure can be applied to the first mask 16 and the second mask 18 to inhibit any of the inert barrier composition from migrating into the protected portion 11.

An inert barrier composition 20 is applied onto the fabric around the portion 11 that is protected by the masks 16, 18. Methods of applying the inert barrier composition 20 can depend on the type of fabric 10, and include but are not limited to gravure, offset gravure, flexographic press, offset press, roll, air knife, brush, meyer rod, silk screen and roller, etc.

The inert barrier composition 20 can be applied to one or both of the surfaces 12, 14 of the fabric 10, depending on the several factors including but not limited to the thickness of the fabric, the viscosity of the inert barrier composition, the composition of either or both the fabric and the inert barrier composition, etc. In one particular embodiment, the inert barrier composition 20 coats both the first surface 12 and the second surface 14, as well as saturates the thickness of the fabric 10 from the first surface 12 to the second surface 14.

Generally, the inert barrier composition 20 includes a cement, which generally comprises a resin and a solvent system. The resin can be composed of any resin suitable for permeating the fabric while remaining inert to the analyte of the sample. In one embodiment, the resin includes a polyvinylchloride (PVC) resin. The solvent system can include any suitable solvent for applying the resin material to the fabric, which may include tetrahydrofuran, methyl ethyl ketone, acetone, cyclohexanone, etc., or mixtures thereof.

The inert barrier composition 20 can be applied to the fabric 10 at any amount sufficient to saturate the thickness of the fabric 10, and upon drying, prevent migration of a liquid sample applied out of the sample area. In particular embodiments, the inert barrier composition 20 is applied at an add-on weight of about 1% to about 10%, such as about 1% to about 5%.

Figure 3:
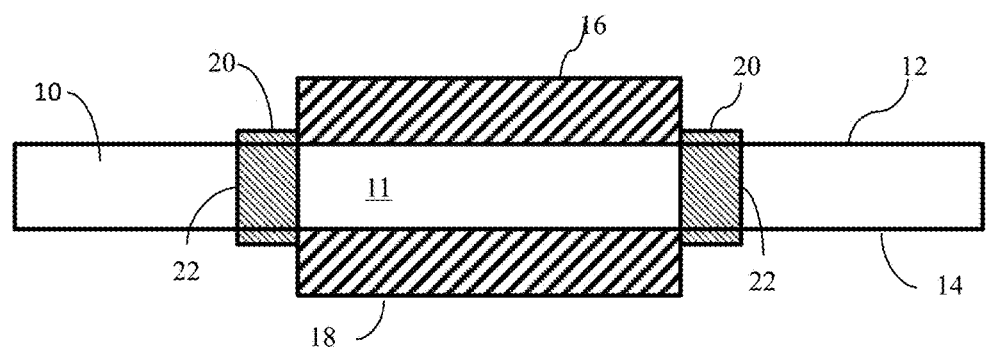
FIG. 3 is a cross-sectional view of the exemplary fabric of FIG. 2 having the mask positioned on either surface of the fabric protecting the sample area and an inert barrier composition onto the fabric around the portion protected.
Figure 4:
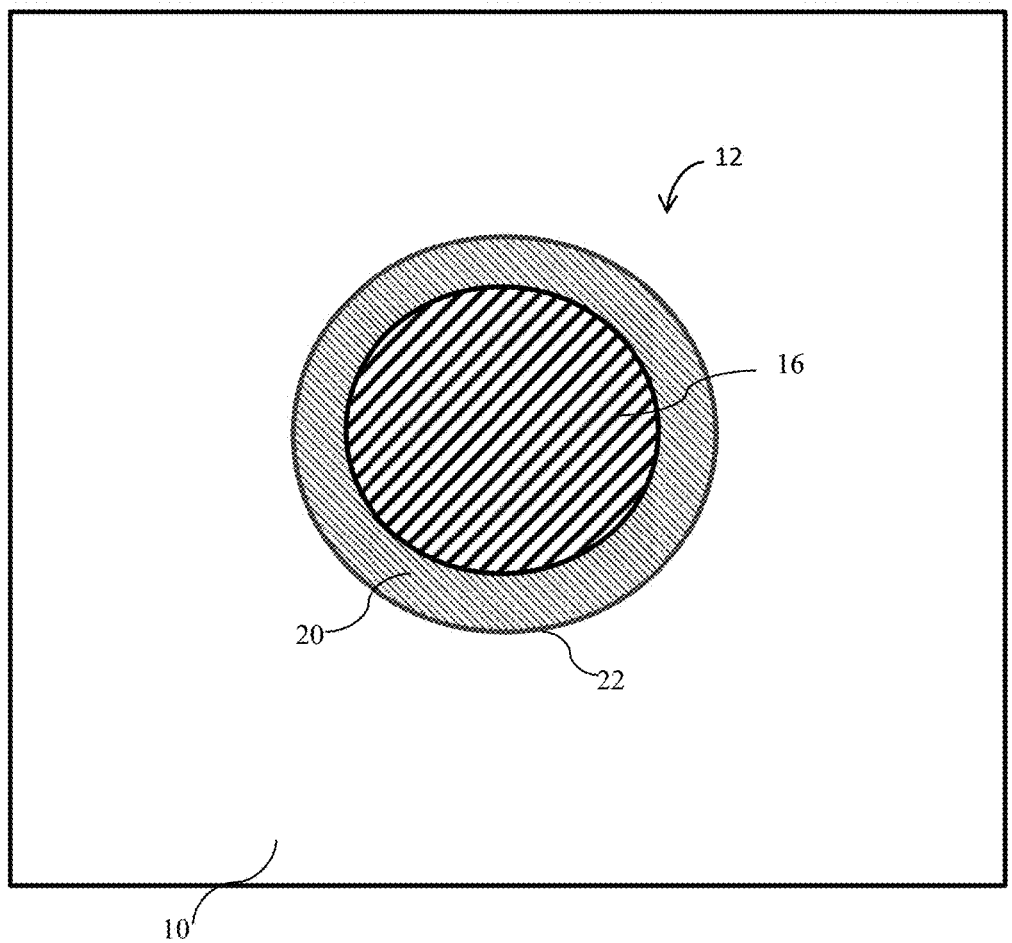
FIG. 4 is a top-down view of the exemplary fabric of FIG. 3 showing the mask positioned on the first surface of the fabric and the inert barrier composition applied onto the fabric around the portion protected.
Figure 5:
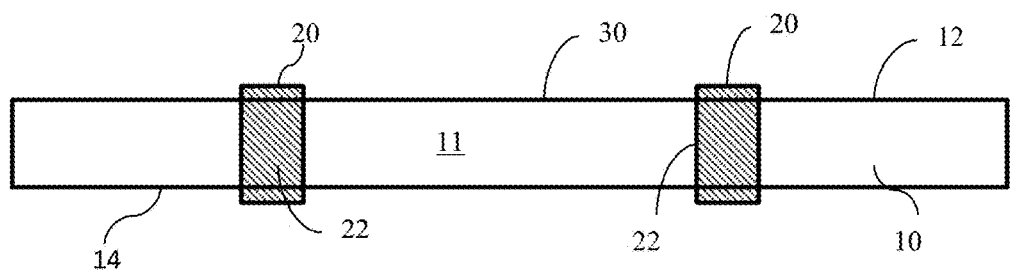
FIG. 5 is a cross-sectional view of the exemplary fabric of FIG. 3 after removing the mask and drying the inert barrier composition to form the inert barrier coating.
Figure 6:
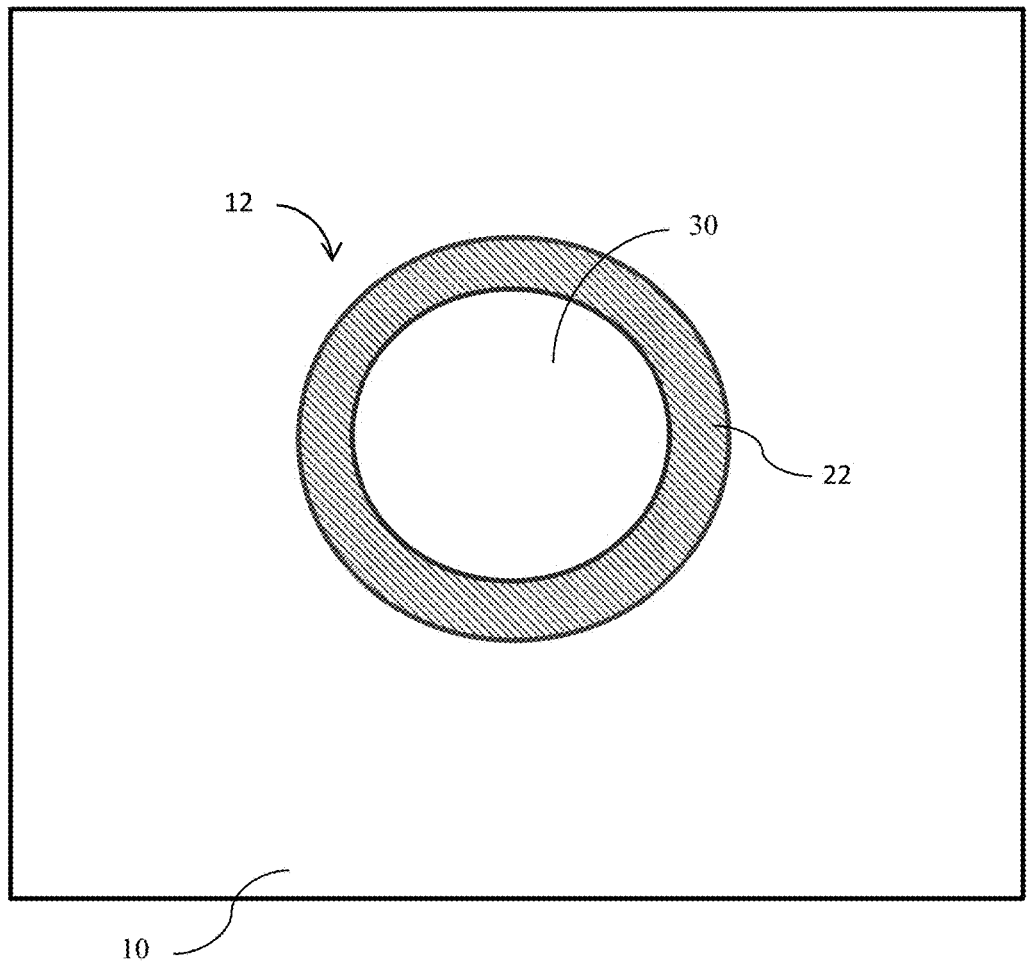
FIG. 6 is a top-down view of the exemplary fabric of FIG. 5.

As shown in FIGS. 3 and 4, the inert barrier composition 20 is then dried to form an inert barrier coating 22 in and on the fabric 10. Drying to remove the solvent system and curing of the inert barrier composition 20 can be accomplished at room temperature (e.g., about 25° C.) or by heating in order to remove the solvent system from the inert barrier composition 20. Heating may be achieved at any suitable temperature depending on the composition of the inert barrier composition 20 and/or the composition of the fabric 10. In most embodiments, drying can be achieved by heating the inert barrier composition up to 100° C. In one particular embodiment, drying is performed prior to removing the masks 16, 18 from the fabric 10.

Once dried, the inert barrier composition 20 completely surrounds the protected portion 11 throughout the thickness of the fabric 10 in order to inhibit any substantial flow of a sample through the inert barrier composition 20 out of the sample area 30.

Although shown as forming a ring, the inert barrier composition 20 can for any suitable shape with any suitable size in the fabric 10.

EXAMPLES

The stain barrier was made up of clear PVC cement (containing tetrahydrofuran, methyl ethyl ketone, acetone, polyvinyl chloride resin, and cyclohexanone) diluted with acetone to a dilution factor of 3:4 to achieve desired viscosity.

Caps taken from laboratory sample vials were used as stencils for stain-barrier application. One cap was placed on each side of a fabric sample so that the open end of the caps face each other with the fabric sample in-between. A C-clamp was used to secure the caps in this position with the maximum amount of pressure allowed without deforming the caps. Using a cotton swab, two coats of the stain-barrier solution were applied to the fabric around the caps on both sides of the fabric sample. The fabric sample was allowed to dry for at least two hours before removal from the clamp and caps.

Figure 1B:
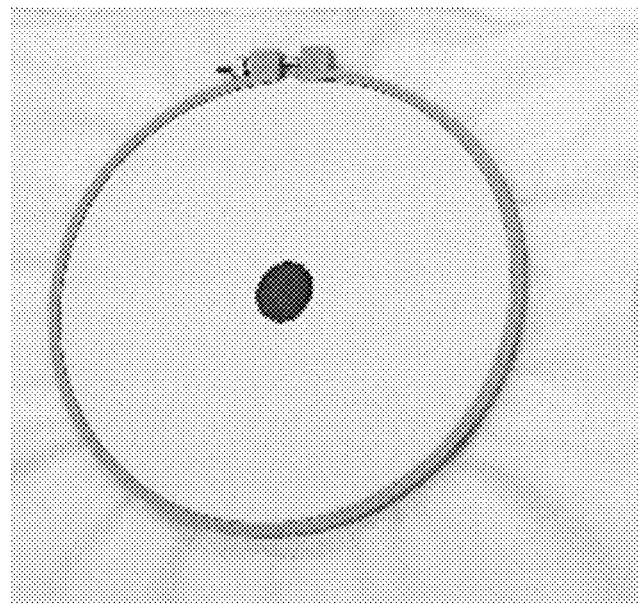
FIG. 1b shows a cotton fabric having a stain applied to a target area unprotected by an inert barrier coating.
Figure 1C:
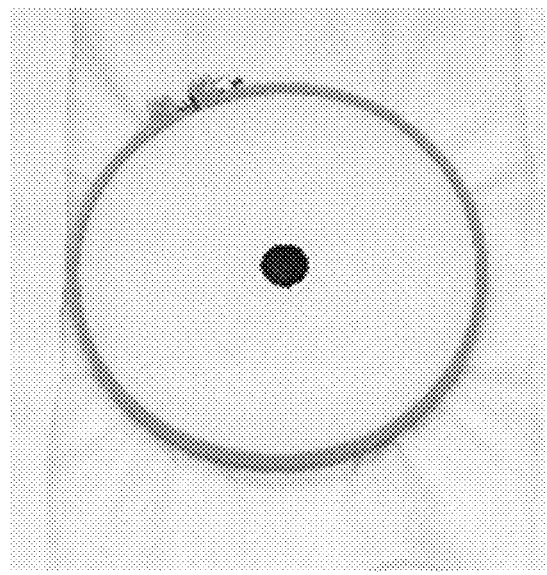
FIG. 1c shows a nylon fabric having a stain applied to a target area protected by an inert barrier coating.
Figure 1D:
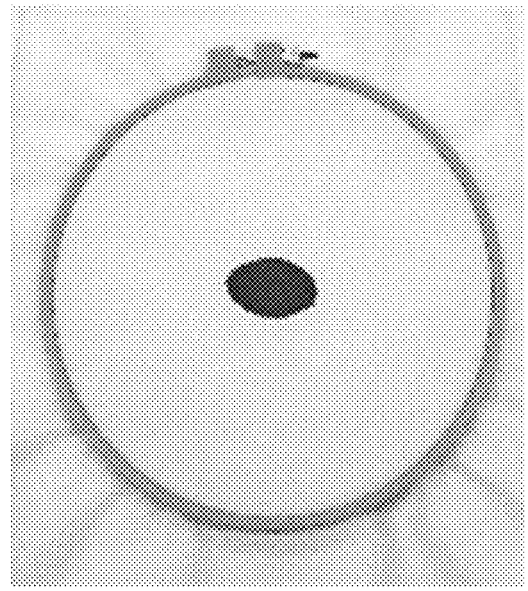
FIG. 1d shows a nylon fabric having a stain applied to a target area unprotected by an inert barrier coating.
Figure 1E:
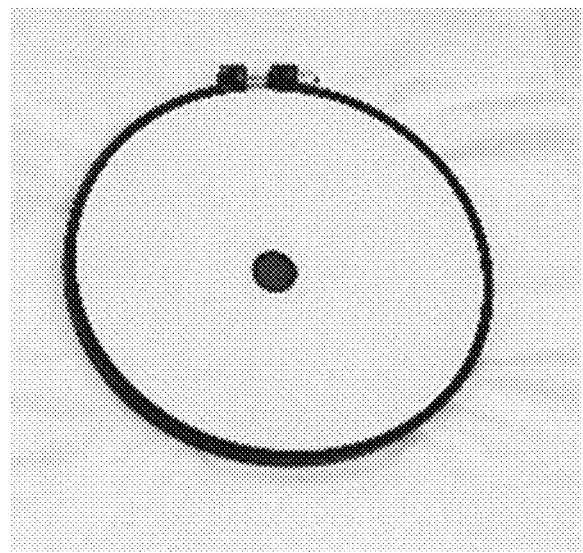
FIG. 1e shows a polyester fabric having a stain applied to a target area protected by an inert barrier coating.
Figure 1F:
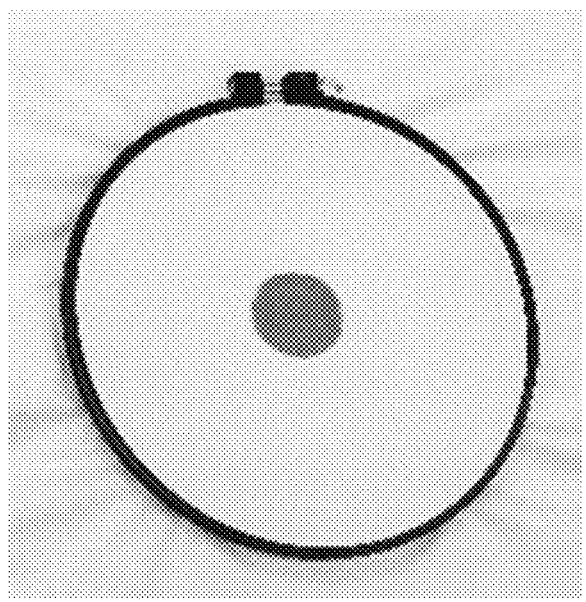
FIG. 1f shows a polyester fabric having a stain applied to a target area unprotected by an inert barrier coating.

Referring to FIGS. 1a, 1c, and 1e, three white fabrics are respectively shown: a cotton fabric, a nylon fabric, and a polyester fabric. Each of the fabric samples of FIGS. 1*a*, 1*c*, and 1*e* had a stain-barrier applied. For comparison, FIGS. 1*b*, 1*d*, and 1*f* respectively shown: a cotton fabric, a nylon fabric, and a polyester fabric. The samples of FIGS. 1*b*, 1*d*, and 1*f* do not have a stain barrier applied.

Fresh, undiluted mouse blood was applied to each fabric using a micropipette. The same amount was applied to all six samples. Clearly, the stains on the bottom vary in size. Since all stains were made using the same amount of blood, stains differing in size also differ in concentration. Therefore, one could not accurately and precisely compare the detection responses of a liquid on different substrates without use of the presently presented stain-barrier.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a sample area on a fabric, the method comprising:
    protecting a portion of the fabric;
    applying an inert barrier composition onto the fabric around the portion protected; and
    drying the inert barrier composition to form an inert barrier coating; and
    exposing the protected portion of the fabric such that the sample area is surrounded by the inert barrier coating.

2. The method of claim 1, wherein the inert barrier coating comprises a cement.

3. The method of claim 2, wherein the cement comprises a resin and a solvent system.

4. The method of claim 3, wherein the resin comprises a polyvinyl chloride resin.

5. The method of claim 4, wherein the solvent system comprises tetrahydrofuran, methyl ethyl ketone, acetone, cyclohexanone, or mixtures thereof.

6. The method of claim 5, wherein the solvent system comprises tetrahydrofuran, methyl ethyl ketone, acetone, and cyclohexanone.

7. The method of claim 1, wherein the fabric defines a first surface and a second opposite surface, and wherein the fabric is protected on the first surface and the second surface.

8. The method of claim 1, wherein the inert barrier composition saturates the fabric around the sample area.

9. The method of claim 1, wherein the fabric defines a first surface and a second opposite surface, and wherein the inert barrier composition is applied to both first surface and the second opposite surface of the fabric.

10. The method of claim 1, wherein the fabric comprises a woven fabric.

11. The method of claim 10, wherein the fabric comprises cotton fibers, nylon fibers, polyester fibers, silk fibers, or mixtures thereof.

12. The method of claim 1, wherein drying the inert barrier composition is achieved at 25° C.

13. The method of claim 1, wherein drying the inert barrier composition is performed by heating the inert barrier composition up to 100° C.

14. The method of claim 1, further comprising:
    applying a blood sample to the sample area, wherein the blood sample saturates the fabric in the sample area but is prevented from migrating out of the sample area by the inert barrier coating.

* * * * *